US006379296B1

(12) United States Patent
Baggett

(10) Patent No.: US 6,379,296 B1
(45) Date of Patent: Apr. 30, 2002

(54) MEDICAL LIGHTING DEVICE

(76) Inventor: Richard W. Baggett, 245 W. Williams Way, Moab, UT (US) 84582

( * ) Notice: Subject to any disclaimer, the term of this patent is extended or adjusted under 35 U.S.C. 154(b) by 0 days.

(21) Appl. No.: 09/277,021

(22) Filed: Mar. 26, 1999

(51) Int. Cl.$^7$ .............................................. A61B 1/06
(52) U.S. Cl. ...................... 600/178; 600/179; 600/249
(58) Field of Search .................. 600/178, 179, 600/180, 160, 199, 200, 249; 607/88, 90

(56) References Cited

U.S. PATENT DOCUMENTS

| | | | | |
|---|---|---|---|---|
| 1,965,865 A | * | 7/1934 | Thomson ...................... | 128/23 |
| 2,017,137 A | * | 10/1935 | Wappler ...................... | 128/23 |
| 2,320,709 A | * | 6/1943 | Arnesen ...................... | 128/17 |
| 2,467,954 A | | 4/1949 | Becker ...................... | 240/10.6 |
| 2,648,762 A | | 8/1953 | Dunkelberger ............. | 240/10.6 |
| 2,649,087 A | | 8/1953 | Allyn et al. ................ | 128/6 |
| 2,793,639 A | | 5/1957 | Roberge ...................... | 128/6 |
| 2,911,968 A | | 11/1959 | Shueler et al. ............... | 128/6 |
| 3,042,022 A | * | 7/1962 | Sheldon ...................... | 600/179 |
| 3,103,723 A | | 9/1963 | Becker ...................... | 24/3 |
| 3,481,325 A | * | 12/1969 | Glassman .................... | 600/179 |
| 3,592,199 A | | 7/1971 | Ostensen .................... | 128/6 |
| 3,595,222 A | * | 7/1971 | Vellacott et al. ............. | 128/11 |
| 3,716,047 A | | 2/1973 | Moore et al. ................. | 128/18 |
| 3,744,481 A | | 7/1973 | McDonald ................... | 128/6 |
| 3,762,400 A | | 10/1973 | McDonald ................... | 128/18 |
| 3,789,835 A | * | 2/1974 | Whitman .................... | 128/17 |
| 3,796,214 A | | 3/1974 | Davis ......................... | 128/20 |
| 3,881,468 A | * | 5/1975 | Foltz ......................... | 128/23 |
| 4,210,133 A | * | 7/1980 | Castaneda ................... | 128/6 |
| 4,347,553 A | | 8/1982 | Saron ......................... | 362/189 |
| 4,546,761 A | | 10/1985 | McCullough ................. | 128/6 |
| 4,566,439 A | | 1/1986 | Burgin ....................... | 128/6 |
| 4,572,164 A | * | 2/1986 | Yoshida et al. ............... | 128/6 |
| 4,597,383 A | | 7/1986 | VanDerBel ................... | 128/18 |
| 4,638,792 A | | 1/1987 | Burgin ....................... | 128/6 |
| 4,759,349 A | * | 7/1988 | Betz et al. ................... | 604/39 |
| 4,778,247 A | | 10/1988 | Carpenter ................... | 350/96.26 |
| 4,823,244 A | * | 4/1989 | Alaybayoglu et al. ....... | 362/194 |
| 4,971,036 A | | 11/1990 | Collins ....................... | 128/17 |
| 5,005,966 A | * | 4/1991 | Handler et al. .............. | 351/221 |
| 5,337,735 A | * | 8/1994 | Salerno ...................... | 128/11 |
| 5,495,286 A | * | 2/1996 | Adair ......................... | 348/68 |
| 5,906,576 A | * | 5/1999 | Upsher ....................... | 600/178 |

FOREIGN PATENT DOCUMENTS

GB            971866        10/1964

* cited by examiner

*Primary Examiner*—Linds C. M. Dvorak
*Assistant Examiner*—Jocelyn Ram
(74) *Attorney, Agent, or Firm*—Mallinckrodt & Mallinckrodt; Robert R. Mallinckrodt

(57) ABSTRACT

A lighting device, particularly suited for medical examination purposes and suited to be attached to a medical examination device such as a vaginal speculum, includes a power source and a flexible, preferably malleable arm extending from the power source with a nondirectional light source at its end. The arm has a small diameter allowing it to be used with medical instruments without blocking the viewing area provided by such instruments and allowing it to be inserted through tubes commonly used in medical, dental, or veterinary procedures. For medical, dental, or veterinary use, the outside temperature of the light source is controlled to keep such temperature below a temperature that would damage living tissue.

12 Claims, 4 Drawing Sheets

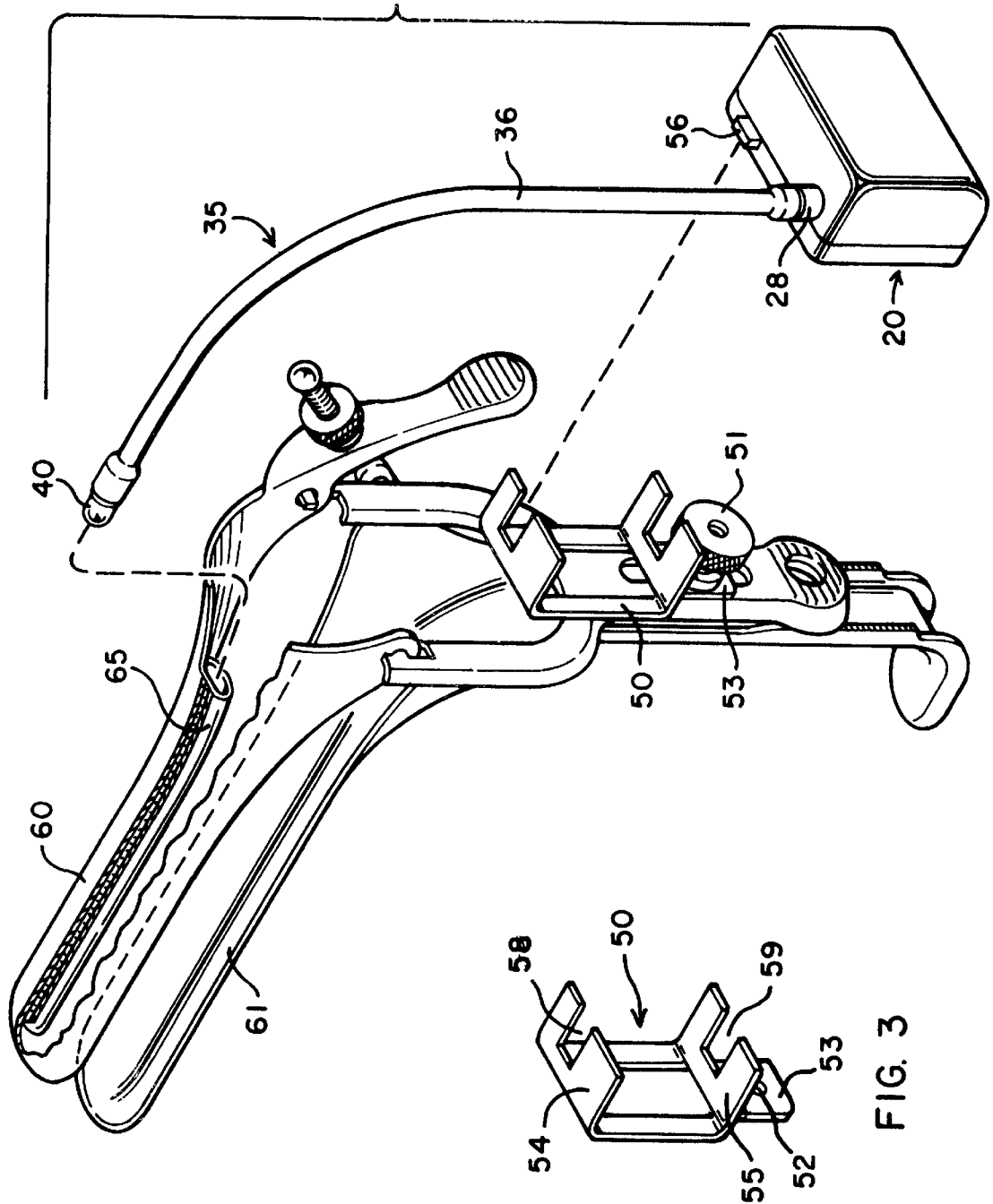

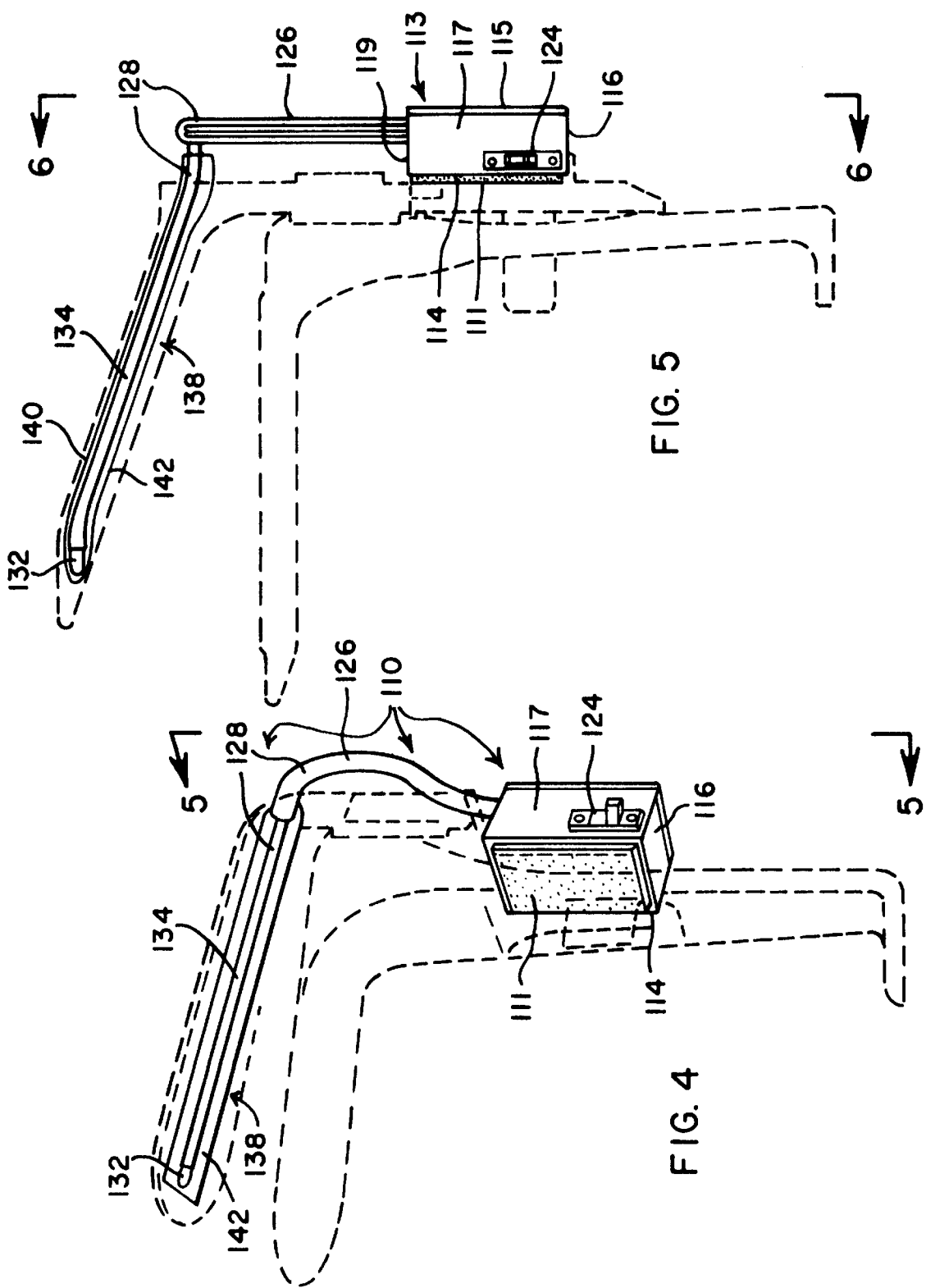

MEDICAL LIGHTING DEVICE

BACKGROUND OF THE INVENTION

1. Field

Figure 1:
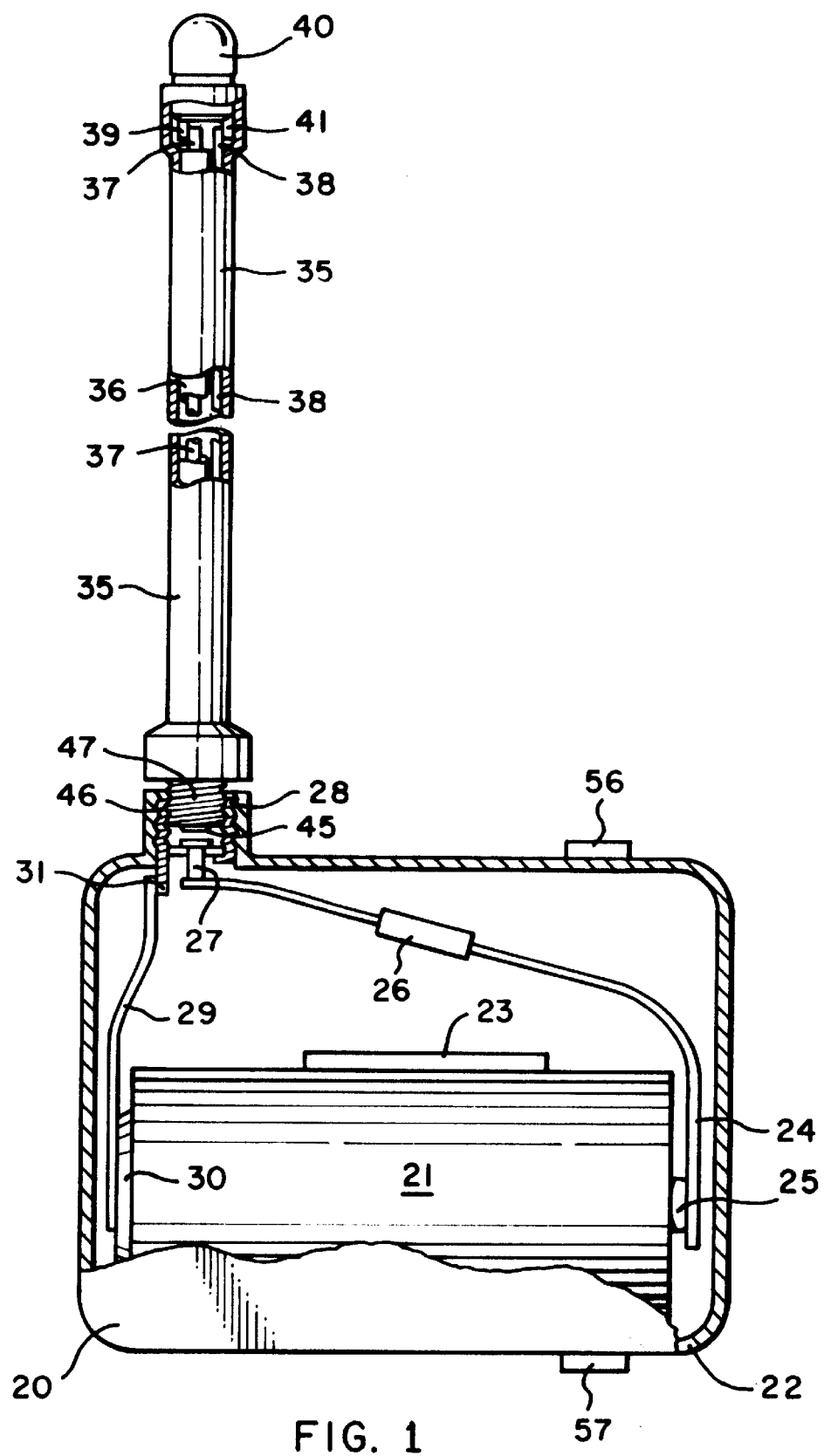

The invention relates to illuminating means for use in examining body cavities and for use with medical instruments for medical examination purposes, such as, but not limited to, a vaginal speculum.

2. State of the Art

Various illuminating means have been employed in the past to illuminate cavities within the human body to facilitate examination thereof or the performance of medical procedures therein. Among these are various light-conductive specula. For example, there is a device disclosed by Moore et al. in U.S. Pat. No. 3,716,047. Although the speculum disclosed by Moore et al. is designed to be made at a cost low enough to warrant discarding after use, it is to be used in conjunction with a nondisposable light source that is not a low-cost item and requires the use of such light source with a speculum specially designed for use therewith. That is, it is not adaptable to a variety of specula. Likewise, the specula disclosed by McDonald in U.S. Pat. No. 3,762,400 and by VanDerBel in U.S. Pat. No. 4,597,383 use non-disposable light sources that are not adaptable to the variety of specula most commonly employed by physicians.

Furthermore, these patented illumination devices and other illumination devices on the market employ projected, directional light. Some commercially available specula have their lighting means disposed on the lower blades of the specula where a heavy discharge, e.g., a vaginal discharge, can pool and obscure the light source. It is desirable to have an illuminating device that can be applied to and employed with the variety of specula and other medical instruments commonly used by medical practitioners and one that uses a global light source instead of projected, directional light. If used with a vaginal speculum, it is further desirable that the light source be disposed adjacent to the upper blade thereof to avoid being obscured by pooled body fluids.

SUMMARY OF THE INVENTION

The lighting device of the invention is adapted particularly for examination of human and other animal body cavities and includes a non-directional, global light source at the end of a flexible and preferably malleable arm that radiates light of brightness sufficient for the examination concerned while the light source remains below a temperature that will damage living tissue. In addition, the lighting device has a light source and extension arm configured to be of relatively small diameter so as to easily be positioned in or along a medical examination device such as a vaginal speculum or fed into a cavity through a tube such as an intubation tube or paralleling a retractor in open wounds.

The device of the invention includes a nondirectional, global light source mounted at the end of a malleable arm which is connected to a case housing a source of power, such as a battery, so that power can be connected to the light source through the arm when illumination of the light source is desired. For most applications, the arm and light source at the end thereof should have a diameter of no more than about three millimeters so that it can easily fit along or through various medical devices such as along an arm of a vaginal speculum without interfering with the viewing area or may be inserted through a tube such as a intubation tube. Further, since the light source may come in contact with or be positioned in close proximity to human or other animal tissue, it is important that the temperature of the light source be limited to a temperature below that which will damage living tissue. Thus, it is preferred that the temperature of the light source be controlled to remain below about 42° C. This can be done by controlling the power supplied to the light source as by inserting a resistor in series between the light source and source of power, and if desired, in addition providing a transparent sheath over the light source. The light source needs to provide enough light for the examination concerned, so if a body cavity examination is being performed, enough light to illuminate the interior of the cavity, or if a dental exam or location determination such as an intubation tube placement is being performed, enough light to shine through a tooth or through the chest and skin. A light output of about 75 foot candles at one-half inch and about 50 foot candles at one inch from the source has been found satisfactory. The light source may conveniently take the form of an incandescent quartz-halogen light of the type used in "mag light" flashlights.

A switch may be provided between the light source and power supply for connecting power when desired to illuminate the light source, or the connection of the arm to the light source can be configured so that when securely connected, such as by screwing the base of the arm tightly into a power source case, the light source is connected. In such case, the light source is disconnected by partially unscrewing the arm from the power source case.

For many applications, the power source case will be removably secured to a medical instrument, such as a vaginal speculum, so that the device, including the arm and light source, are secured to and become part of the instrument. For use with a vaginal speculum, the invention includes a special clip which is secured to the speculum and which removably holds the power source case, and in turn the arm and light source, to the speculum so that the doctor can use the speculum in normal manner, except that the lighting device of the invention is provided as a part thereof and aids in the examination.

While it is currently preferred that the arm be malleable throughout its length, for some applications, the arm may include a rigid portion extending from the power source case with a malleable portion holding the light source at its distal end. Thus, the device may be attached to a medical instrument as part of a light-providing instrument and still be subject to deformation suitable to the task at hand as may be required or desired by the physician, surgeon, or other medical practitioner using the device. For use with a speculum or similar instrument, the rigid portion of the arm is formed to extend around the viewing channel of the instrument, thus saving the physician the step of forming this portion of the arm. The malleable portion is bent to extend along a blade of the speculum to locate the global light source deep within the cavity to be illuminated and out of the way of the physicians view and any pooled body fluids. Having a global light source located deep within a cavity provides illumination far superior to that of the projected, directional light sources of the prior art.

The entire device can be constructed to be moisture resistant and, thus, easily sterilized, unlike some prior art illumination devices. However, to enable the reuse of the lighting device without sterilization, the malleable portion of the arm can be provided with an elongate, flat, disposable covering or sheath having elongate top and bottom walls attached together along the sides and distal ends of such walls, leaving an opening at the proximal end of the covering for the insertion therein of the light source and arm. At least the distal end of such covering is transparent.

Advantageously, the covering has a strip of adhesive along an outside wall for removably securing the covering to a blade of the speculum or to other instruments. It is further advantageous to provide the covering with a lip extending from the bottom wall at the opening to facilitate insertion of the malleable portion of the arm.

THE DRAWINGS

Figures 6, 7:
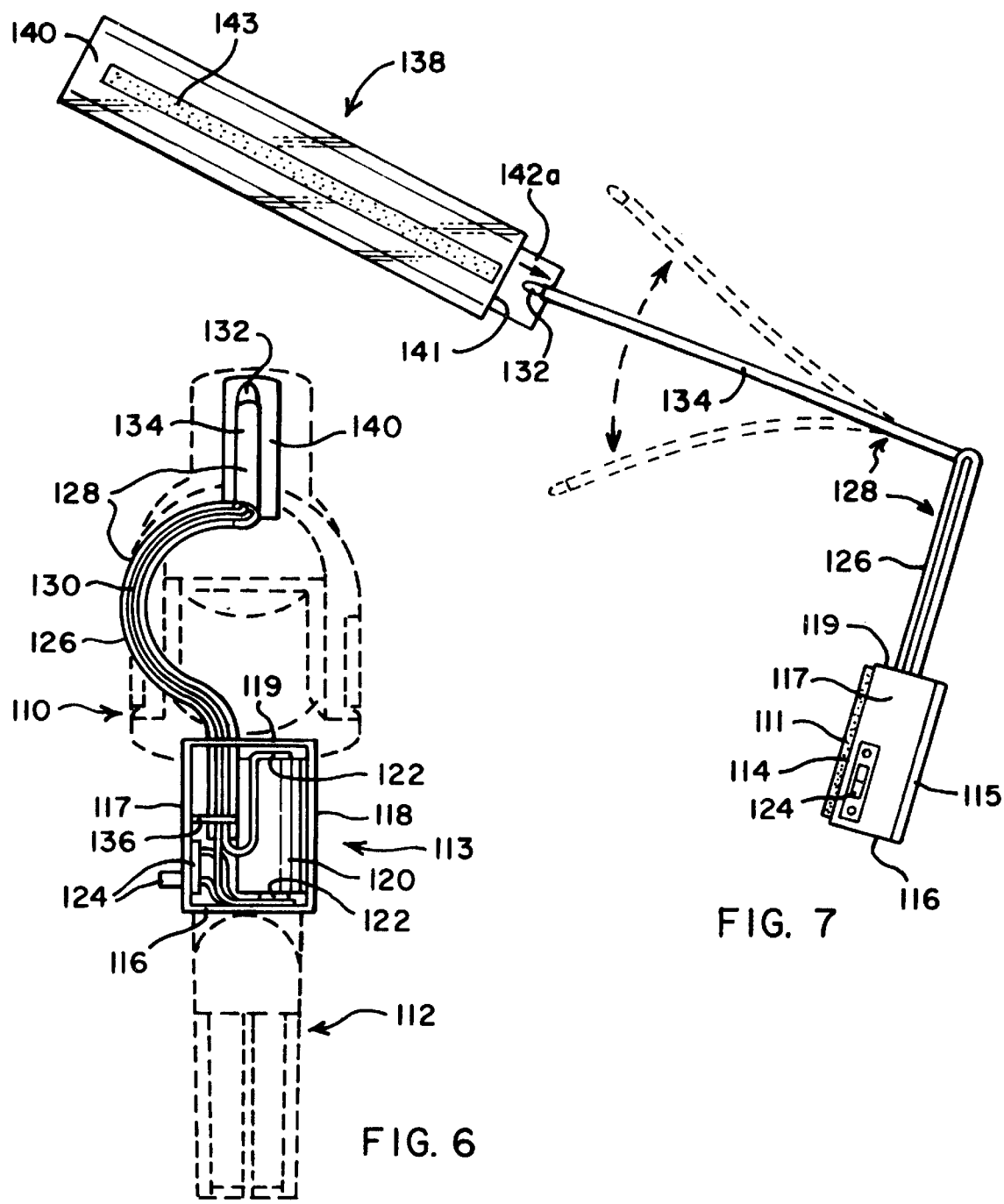

The best mode presently contemplated for carrying out the invention is illustrated in the accompanying drawings, in which:

FIG. 1 is a front elevation of a lighting device of the invention with portions broken away to show interior parts;

FIG. 2, a perspective assembly view of a vaginal speculum showing how the lighting device of the invention fits onto the speculum;

FIG. 3, a perspective view of the clip which holds the lighting device to the speculum;

FIG. 4, a perspective view of a second embodiment of a lighting device according to the invention attached to a speculum indicated by broken lines;

FIG. 5, a side elevation taken along the line 5—5 of FIG. 4;

FIG. 6, a view in front elevation taken along the line 6—6 of FIG. 5, the rear wall of the container for the power source being removed to show the arrangement of components inside the case; and FIG. 7, a view in side elevation of the lighting device and covering of FIGS. 4–6, but removed from the speculum.

DETAILED DESCRIPTION OF THE ILLUSTRATED EMBODIMENT

The lighting device of the invention includes a power source case 20 having a power source in the form of a battery 21 therein positioned between case wall 22 and tab 23, FIG. 1. Battery contact 24 contacts positive terminal 25 and extends to connection with power limiting resistor 26 which is connected to the center terminal 27 of screw socket 28. Battery contact 29 extends from contact with the negative terminal end 30 of battery 21 to the outside terminal 31 of screw socket 28.

Malleable arm 35 includes a sleeve 36 of flexible plastic material, such as a heat shrink material, covering copper wire 37 and a smaller wire 38. Copper wire 37 is electrically connected to one lead 39 of light bulb 40 at the distal end of arm 35 and wire 38 is electrically connected to the other lead 41 of light bulb 40. The electrical connections may be solder connections, wire wrap connections, or other satisfactory connections. Wires 37 and 38 are electrically connected in any satisfactory manner to center terminal 45 and outside terminal 46 of male screw connector 47 at the proximal end of arm 35. Male screw connector 47 screws into socket 28 to connect malleable arm 35 to power source case 20. With the arm partially screwed into socket 28 as shown, center contact 45 does not make electrical contact with center terminal 27 so no power is supplied to light bulb 40. When arm 35 is securely screwed into socket 28, contact 45 makes electrical contact with center socket terminal 27 and power from battery 21 is supplied to light bulb 40 to cause illumination of light bulb 40. The arm can be partially unscrewed to the position shown when illumination of bulb 40 is no longer needed. The malleability of arm 35 is provided by the copper wire 37 which may be a fourteen gauge solid wire which is malleable and provides arm 35 with its malleability. This wire and the arm can be bent to any desired configuration and will hold that configuration until changed by a user. In some instances, small gauge wire will work satisfactorily to provide the desired malleability, and in other instances, larger gauge will be desirable.

One purpose of the lighting device of the invention is to provide light in body cavities for medical examination purposes. For example, the light bulb 40 may be used with a vaginal speculum for providing light for a vaginal examination, may be inserted through an intubation tube to illuminate the trachea and lungs which allows a doctor precise placement of the intubation tube, may be inserted in the mouth behind the teeth to shine through the teeth to show decay and other dental problems, or may be inserted into various other human or other animal body cavities for examination or locating purposes. Because the light bulb or any other light source used may come in contact with living tissue, it is important in the invention that the outside or exposed temperature of the light bulb be below a temperature that will damage living tissue. For this purpose, it has been found that the temperature of the exposed surface of the light bulb 40 should be no greater than about 42° C. (107.6° F.). It has been found that by limiting the power supplied to bulb 40, the desired temperature can be maintained with satisfactory light output. In the embodiment shown, light bulb 40 may be an incandescent quartz-halogen lamp of T1 configuration such as currently used in "mag" light flashlights. Battery 21 may be a three volt lithium battery. Resistor 26 limits power to the light bulb 40 and may be a low value resistor such as a one or two ohm resistor. With this arrangement, the outside surface temperature of the light bulb 40 remains at about 42° C. Such a bulb at those operating conditions produces about seventy-five foot candles at one-half inch from the bulb, about fifty foot candles at one inch and about forty foot candles at two inches. Where a sheath is used to cover the light bulb during use of the device, the outside or exposed surface of the sheath may be considered as the outside or exposed surface of the light source and as long as such exposed surface is no greater than about 42° C., the outside surface of the light bulb itself may be of higher temperature. Of course, the sheath must be able to withstand the temperature of the light bulb without melting. A polypropylene sheath has been found satisfactory and reduce the temperature of the light source by about 1° C.

It is also important that arm 35 and light bulb 40 be relatively small in diameter so arm 35 can be positioned with respect to medical instruments such as a vaginal speculum so as not to interfere with the viewing of the cavity being examined and so that the arm and light source to be inserted through commonly used tubing such as intubation tubes. Generally, the diameter of the arm and bulb should be no more than about three millimeters in diameter.

In order to attach the lighting device to a medical instrument such as a vaginal speculum, a bracket 50, FIGS. 2 and 3, configured to hold power source case 20 is attached to the instrument, a vaginal speculum being shown in FIG. 2, such as by a screw 51 or similar fastener passed through hole 52 in tab 53 and into the instrument. Tabs 54 and 55 are spaced to snugly receive power source case 20 therebetween with case tabs 56 and 57 extending from opposite sides of case 20 received in positioning openings 58 and 59. Case 20 is frictionally held securely, but removably, in position in bracket 50. In the vaginal speculum shown, screw 51 is a normally present adjusting screw for tightening the base of blades 60 and 61 of the speculum a desired distance apart. In order to light the desired area for viewing using the speculum, the light bulb 40 is positioned near the tip of upper blade 60 by extending arm 35 along the underside (inside) of upper blade 60. The upper blade is preferred so that the light does not get covered and obscured by discharges of vaginal fluids.

In order to eliminate the need to sterilize or clean the arm after each use, it is preferred that a removable plastic sheath 65 cover the arm. Such sheath is preferably secured to the underside of upper blade 60. Securement may be done with a strip of pressure sensitive adhesive or tape which preferably is supplied as part of the sheath. When the sheath is secured to the instrument, it also helps hold the arm in desired position. At least the tip of the sheath should be substantially transparent to transmit light from light bulb 40.

An alternate embodiment of the lighting device of the invention is shown in FIGS. 4–7. In this embodiment, the light device includes a substantially rigid portion of the arm extending from the power source case with a malleable portion extending from the end of the substantially rigid portion to the tip of the arm. Thus, the arm includes a substantially rigid portion and a malleable portion.

As illustrated, device 110 is attached by attachment means, here shown as an adhesive covered strip 111, such as a foam strip with pressure sensitive adhesive on both sides, to a conventional plastic or metal vaginal speculum 112, which is indicated schematically by broken lines. Various other mounting means could be used. The lighting device includes a power supply case 113 having relatively broad front wall 114 and corresponding rear wall 115 and relatively narrow side walls 116, 117, 118, and 119. The case 113 holds a power source in the form of a battery 120 with means for electrically connecting the light source to the power source, here shown as electrical connections 122, a switch 124, and a part of the rigid portion 126 of an arm 128. Since this portion of the arm is adapted to be connected to the power source case, it is designated the proximal end of the arm. In this embodiment, a switch 124 is operably interconnected with and controls supply of electric current to the light source from the battery. Battery 120 fits snugly in case 113 alongside the aforesaid part of the rigid portion 126 of arm 128.

As in the first embodiment described, arm 128 is slender and elongate and connects, by means of wiring 130, a light bulb 132 with battery 120. Rigid portion 126 of arm 128 is preferably a tube of a hard, non-malleable plastic, although other materials such as metal can be used. Wires 130 run within the tube from battery 120 to the malleable portion 134 of arm 128. Malleable portion 134 also includes a tube, but of a flexible plastic. The wires continue through malleable portion 134 of arm 128 to its distal end, where light bulb 132 is electrically connected thereto.

As shown in FIG. 5, the rigid portion 126 of arm 128 passes through a hole in side wall 119 of case 113. In this instance, the end of a bracket 136 is fastened to side wall 117, FIG. 6, inside case 113. Its other end is bifurcated and attached, as by glue, to rigid portion 126 of arm 128. By virtue of its attachment to bracket 136 and its snug insertion through the hole in side wall 119, rigid portion 126 is substantially fixedly attached to case 113. Rigid portion 126 of arm 128 extends from case 113 taking a curved path, FIGS. 4 and 6, which follows the perimeter of the viewing channel of the speculum. Rigid portion 126 can be molded to follow the shape of any particular speculum or any other medical instrument with which the device is to be used.

The malleable portion 134 of arm 128, includes malleable fourteen gauge copper wire (not shown) within the tube. The copper wire can be bent to any desired shape and holds that shape to fit a variety of specula or other medical instruments or simply to advantageously position the light bulb with respect to an object to be illuminated.

A disposable, elongate, flat covering 138 covers malleable portion 134 of the arm and is preferably secured to the top blade of the speculum, as best shown in FIGS. 4 and 5. The covering 138 is made up of a thin plastic top wall 140 and a similar bottom wall 142 attached together along the sides and distal ends thereof so as to define an opening 141 at the proximal end. Preferably, the covering includes a lip 142a which is a part of bottom wall 142 and extends from the opening to facilitate insertion therein of malleable portion 132 of arm 128. In this instance, covering 138 has attachment means, here in the form of adhesive 143, on the outside portion of its top wall for adhering the cover to the blade of the speculum. At least the distal end of the cover is transparent. Such distal end is where the light bulb 132 is located and can be clear or colored depending on the quality of light desired for specific applications. Such a covering could be a sleeve as shown in U.S. Pat. No. 4,165,000 or U.S. Pat. No. 4,136,776 but made of polypropylene or temperature resistant material Further, if desired, the light bulb could be coated with a plastic material, such as by dipping, to provide color to the light or protect the bulb against possible breakage.

The lighting device constructed according to the invention is inexpensive to manufacture. It can be reused until either the battery is depleted or the bulb burns out and may then be discarded. Alternatively, the device can be returned to the manufacturer for replacement or charging of the battery or replacement of the light bulb. Of course, if desired, the case could be configured to be opened by a user for replacement or recharging of the battery.

The device can be easily attached to popular types of specula presently in use as well as to other medical instruments, such as retractors, to illuminate cavities or wounds, can be inserted into cavities such as the mouth behind the teeth and gums so that light shines therethrough, or may be inserted through tubes inserted into a body to light cavities therein or to shine through the body to indicate position of the light or tube or to aid in examination of the body by illuminating the body between the location of the light source and the observer.

With the lithium battery, resistor, and the quartz-halogen light bulb described, the battery will last for about four and one-half to five hours of continuous use. Also, under such conditions, the battery will discharge and the light go out slowly, rather than suddenly providing no light. With intermittent use, battery life is longer. With use of the resistor to reduce power to the light bulb, light bulb life is significantly increased.

While a malleable arm is presently preferred because it can be bent to a desired shape, and will maintain such shape, when a sheath is secured to the instrument or a channel for the arm is provided in the instrument, the arm may be merely flexible to be inserted into and conform to the sheath or channel, and does not have to be malleable. Further, a sheath need not be attached to an instrument and an instrument need not be used with the device as when, for example, the light is positioned in a mouth. For such use, the arm is bent as desired and is positioned as desired in the mouth by holding the power source case. A sheath may merely be placed over the arm for sterility purposes and/or to keep the arm and light bulb clean. The arm can be made in various lengths as desired depending upon the intended use. For most vaginal speculums, an arm about seven inches in total length has been found satisfactory.

While the lighting device was developed for medical uses, it can be used for other purposes whenever a small global light source is needed, or a global light source is needed to extend through a small access opening.

While the power source has been described as a battery, and a battery is preferred because of portability, the power source could be any means such as a transformer, or merely wiring, to connect power to the arm, and could be a wire extending from the case to a standard electrical wall outlet.

Whereas this invention is here illustrated and described with reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

What is claimed is:

1. A combination lighting device and vaginal speculum, wherein the light source generates heat and has an outside temperature, comprising:

a nondirectional global light source;

a source of power coupled to the light source to cause illumination of the light source;

means for limiting the outside temperature of the light source to a temperature that will not burn tissue;

a vaginal speculum having a speculum blade with a tip; and means for securing the light source in a substantially unblocked position at the tip of the speculum blade whereby nondirectional light from the light source radiates nondirectionally from the tip of the blade during a vaginal examination.

2. A combination lighting device and vaginal speculum according to claim 1, wherein the outside temperature of the light source is limited to a maximum temperature of about 42° C.

3. A combination lighting device and vaginal speculum according to claim 2, wherein the means for limiting the outside temperature of the light source includes means for limiting the power supplied to the light source.

4. A combination lighting device and vaginal speculum according to claim 3, wherein the means for limiting the outside temperature of the light source includes substantially transparent sleeve means at least partially covering the light source.

5. A combination lighting device and vaginal speculum according to claim 3, wherein the means for limiting the outside temperature of the light source includes a resistor electrically in series between the light and the source of power.

6. A combination lighting device and vaginal speculum according to claim 2, wherein the means for limiting the outside temperature of the light source includes substantially transparent sleeve means at least partially covering the light source.

7. A combination lighting device and vaginal speculum according to claim 1, wherein the light source produces about 75 to 80 foot candles of light at a distance of one-half inch from the light source.

8. A combination lighting device and vaginal speculum according to claim 1, wherein the means for securing the light source at the tip of the speculum blade is a malleable arm extending between the source of power and the light source.

9. A combination lighting device and vaginal speculum according to claim 8, wherein the arm includes a malleable wire therein extending the length of the arm and the malleable wire provides the malleability to the arm.

10. A combination lighting device and vaginal speculum according to claim 8, wherein the malleable arm and the light source have maximum diameters of three millimeters.

11. A combination lighting device and vaginal speculum according to claim 1, wherein the means for securing the light source at the tip of the speculum blade includes a substantially rigid portion and a malleable portion.

12. A lighting device for use with a vaginal speculum, comprising:

an electrical power source;

a power source case housing said electrical power source;

a light bulb;

means controllably electrically connecting said electrical power source with said light bulb;

a slender elongate arm connecting said light bulb to the power source case so a s to locate the light bulb distally therefrom, said arm including an elongate rigid portion and an elongate malleable portion, said rigid portion being connected to said case and adapted to extend said rigid portion around the viewing channel of a vaginal speculum, said malleable portion being connected proximally to said rigid portion and having said light bulb connected to its distal end and being capable of being easily and repeatedly bent by hand to any desired shape and holding that shape until bent again;

attachment means adapted for affixing said case to the handle of a vaginal speculum; and an elongate, flat covering for the malleable portion of said elongate arm having a top wall and a bottom wall attached together along the sides and distal ends of said walls leaving an opening at the proximal end, at least the distal end of said covering being transparent, said covering having attachment means along the outside of the top wall adapted for removably securing the covering to the blade of said speculum.

* * * * *